US009170204B2

(12) United States Patent
Park et al.

(10) Patent No.: US 9,170,204 B2
(45) Date of Patent: Oct. 27, 2015

(54) OPTICAL HEADS AND SEQUENCING APPARATUSES INCLUDING THE SAME

(71) Applicant: Samsung Electronics Co., Ltd., Suwon-Si, Gyeonggi-Do (KR)

(72) Inventors: Yoon-dong Park, Osan-si (KR); Kyoung-won Na, Seoul (KR); Sung-dong Suh, Seoul (KR); Beom-suk Lee, Yongin-si (KR); Dong-mo Im, Jindo-gun (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 221 days.

(21) Appl. No.: 13/777,190

(22) Filed: Feb. 26, 2013

(65) Prior Publication Data
US 2013/0224847 A1 Aug. 29, 2013

(30) Foreign Application Priority Data
Feb. 29, 2012 (KR) ........................ 10-2012-0021405

(51) Int. Cl.
*C12M 1/34* (2006.01)
*C12M 3/00* (2006.01)
*G01N 21/75* (2006.01)
*G01N 35/00* (2006.01)
*G01N 21/64* (2006.01)

(52) U.S. Cl.
CPC .......... *G01N 21/75* (2013.01); *G01N 35/00069* (2013.01); *G01N 2021/6421* (2013.01)

(58) Field of Classification Search
CPC .......... G01N 2021/6421; G01N 21/75; G01N 35/00069

USPC ............................................ 435/283.1–309.4
See application file for complete search history.

(56) References Cited

U.S. PATENT DOCUMENTS

| 6,030,581 A * | 2/2000 | Virtanen ...................... 422/68.1 |
| 6,542,455 B1 | 4/2003 | Kuwahara et al. |
| 6,623,696 B1 | 9/2003 | Kim et al. |
| 7,582,261 B2 | 9/2009 | Fuji |

(Continued)

FOREIGN PATENT DOCUMENTS

| JP | 4231920 B2 | 3/2009 |
| KR | 10-0747647 B1 | 8/2007 |

(Continued)

*Primary Examiner* — Nathan Bowers
*Assistant Examiner* — Lydia Edwards
(74) *Attorney, Agent, or Firm* — Harness, Dickey & Pierce, PLC

(57) ABSTRACT

A sequencing apparatus may include a bio-disk having reaction regions in which nucleic acids are polymerized; a stage configured to revolve around an axis, the stage including optical heads for detecting lights emitted from the plurality of reaction regions due to the polymerization of the nucleic acids; and/or a control unit configured to generate data regarding base sequences of the nucleic acids in the reaction regions based on wavelengths of the lights detected by the plurality of optical heads. An optical head may include a light emitting unit configured to emit light toward a reaction region in which nucleic acids are polymerized; a light receiving unit configured to receive the light emitted by the light emitting unit; a de-multiplexing unit configured to de-multiplex the light received by the light receiving unit; and/or a plurality of photoelectric converting units configured to convert the de-multiplexed light to electrical signals.

5 Claims, 8 Drawing Sheets

(56) References Cited

U.S. PATENT DOCUMENTS

2002/0076804 A1* 6/2002 Sheppard et al. .......... 435/287.1
2006/0187459 A1 8/2006 Ok et al.
2010/0210952 A1* 8/2010 Taira et al. .................. 600/476

FOREIGN PATENT DOCUMENTS

| KR | 10-0830926 | B1 | 5/2008 |
| KR | 20090078683 | A | 7/2009 |
| KR | 10-0992553 | B1 | 11/2010 |

* cited by examiner

OPTICAL HEADS AND SEQUENCING APPARATUSES INCLUDING THE SAME

CROSS-REFERENCE TO RELATED APPLICATION(S)

This application claims priority from Korean Patent Application No. 10-2012-0021405, filed on Feb. 29, 2012, in the Korean Intellectual Property Office (KIPO), the entire contents of which are incorporated herein by reference.

BACKGROUND

1. Field

Example embodiments of the inventive concept may relate to optical heads and/or sequencing apparatuses including the same. Example embodiments of the inventive concept also may relate to optical heads manufactured by using silicon photonics technology and/or sequencing apparatuses including a plurality of the optical heads.

2. Description of Related Art

In a deoxyribonucleic acid (DNA) sequencing method in the related art, the base sequence of DNA is analyzed by using a large and expensive apparatus which captures a light emitted during a polymerase chain reaction of DNA by using fluorescent materials. In this case, it is necessary to use an image capturing apparatus, such as a charge coupled device (CCD). However, operation of such an image capturing apparatus is slower than DNA cloning speed, and thus a method using an image capturing apparatus features a high error ratio.

SUMMARY

Example embodiments of the inventive concept may provide sequencing apparatuses that feature a low error ratio by performing nucleic acid sequencing without using image capturing apparatuses.

Example embodiments of the inventive concept also may provide optical heads suitable for the sequencing apparatus.

In some example embodiments, a sequencing apparatus may comprise a bio-disk having arranged thereon a plurality of reaction regions in which nucleic acids are polymerized; a stage configured to revolve around a revolving axis, the stage including a plurality of optical heads for detecting lights emitted from the plurality of reaction regions due to the polymerization of the nucleic acids; and/or a control unit configured to generate data regarding base sequences of the nucleic acids in the plurality of reaction regions based on wavelengths of the lights detected by the plurality of optical heads.

In some example embodiments, the plurality of optical heads may comprise a plurality of first optical heads. The plurality of first optical heads may be arranged to be a same distance apart from the revolving axis.

In some example embodiments, the plurality of reaction regions may comprise a plurality of first reaction regions that are arranged to be a first distance apart from a center of the bio-disk and are arranged in a circumferential direction. The plurality of optical heads may comprise a plurality of first optical heads that are arranged to be the first distance apart from the revolving axis and are arranged in the circumferential direction. The plurality of first optical heads may be configured to rotate around the revolving axis and are configured to detect lights emitted by the plurality of first reaction regions.

In some example embodiments, the plurality of reaction regions may further comprise a plurality of second reaction regions that are arranged to be a second distance, which is different from the first distance, apart from the center of the bio-disk and are arranged in the circumferential direction. The plurality of optical heads may further comprise a plurality of second optical heads that are arranged to be the second distance apart from the revolving axis and are arranged in the circumferential direction. The plurality of second optical heads may be configured to rotate around the revolving axis and to detect light emitted by the plurality of second reaction regions.

In some example embodiments, polymerase may be attached to each of the plurality of reaction regions. The polymerase may attach four types of nucleotides that are respectively marked with four types of fluorescent materials to a template strand using base-pairing interactions and/or may separate the fluorescent materials from the nucleotides. Lights emitted by the four types of fluorescent materials may have different wavelengths.

In some example embodiments, each of the optical heads may comprise a silicon photonic device.

In some example embodiments, each of the optical heads may comprise a de-multiplexing unit configured to de-multiplex light emitted by the plurality of reaction regions according to wavelengths thereof, and/or a plurality of photoelectric converting units configured to convert de-multiplexed light to electrical signals.

In some example embodiments, each of the optical heads may comprise a light emitting unit configured to emit light, and/or an orienting unit configured to orient light emitted by the light emitting unit toward the plurality of reaction regions.

In some example embodiments, an optical head may comprise a light emitting unit configured to emit light toward a reaction region in which nucleic acids are polymerized, a light receiving unit configured to receive the light emitted by the light emitting unit and that has one from among first through fourth wavelengths, a de-multiplexing unit configured to de-multiplex the light received by the light receiving unit according to wavelengths thereof, and/or a plurality of photoelectric converting units configured to convert the de-multiplexed light to electrical signals.

In some example embodiments, the light emitting unit may comprise a light emitting diode (LED) configured to emit the light toward the reaction region, a first grating coupler configured to orient the light emitted by the LED toward the reaction region, and/or a first waveguide configured to transmit the light emitted by the LED to the first grating coupler.

In some example embodiments, the light receiving unit may comprise a second grating coupler configured to receive light emitted by the reaction region, and/or a second waveguide configured to transmit the light received by the second grating coupler to the de-multiplexing unit.

In some example embodiments, the de-multiplexing unit may comprise an arrayed waveguide grating configured to separate light received by the light receiving unit according to wavelengths thereof.

In some example embodiments, the arrayed waveguide gratings may comprise a first slab waveguide connected to a second grating coupler via a waveguide, first through fourth waveguide gratings that are connected to the first slab waveguide and have different lengths, a second slab waveguide to which the first through fourth waveguide gratings are connected, and/or first through fourth output waveguides that are connected to the second slab waveguide from different locations. The first through fourth output waveguides may be respectively connected to the plurality of photoelectric converting units.

In some example embodiments, the de-multiplexing unit may comprise a circular filter configured to separate the light received by the light receiving unit according to wavelengths thereof.

In some example embodiments, the light receiving unit may comprise a second grating coupler configured to receive light emitted by the reaction region, and/or wherein the circular filter may comprise a first waveguide connected to a second grating coupler, four ring structures that are respective distances corresponding to first through fourth wavelengths apart from the first waveguide, and/or four second waveguides that are respective distances corresponding to the first through fourth wavelengths apart from the four ring structures and are connected to the plurality of photoelectric converting units.

In some example embodiments, an optical head may comprise a reaction region configured to allow nucleic acids to be polymerized, a light emitting unit configured to emit light toward the reaction region; a light receiving unit configured to receive light from the reaction region, a de-multiplexing unit configured to de-multiplex the light received by the light receiving unit according to wavelengths of the received light, and/or a plurality of photoelectric converting units configured to convert the de-multiplexed light to electrical signals.

In some example embodiments, the light emitting unit may comprise a first grating coupler configured to orient the light emitted by the light emitting unit toward the reaction region, and/or a first waveguide configured to transmit the light emitted by the light emitting unit to the first grating coupler.

In some example embodiments, the light receiving unit may comprise a second grating coupler configured to receive the light from the reaction region, and/or a second waveguide configured to transmit the light received by the second grating coupler to the de-multiplexing unit.

In some example embodiments, the de-multiplexing unit may comprise an arrayed waveguide grating configured to separate the light received by the light receiving unit according to the wavelengths of the received light.

In some example embodiments, the de-multiplexing unit may comprise a circular filter configured to separate the light received by the light receiving unit according to the wavelengths of the received light.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
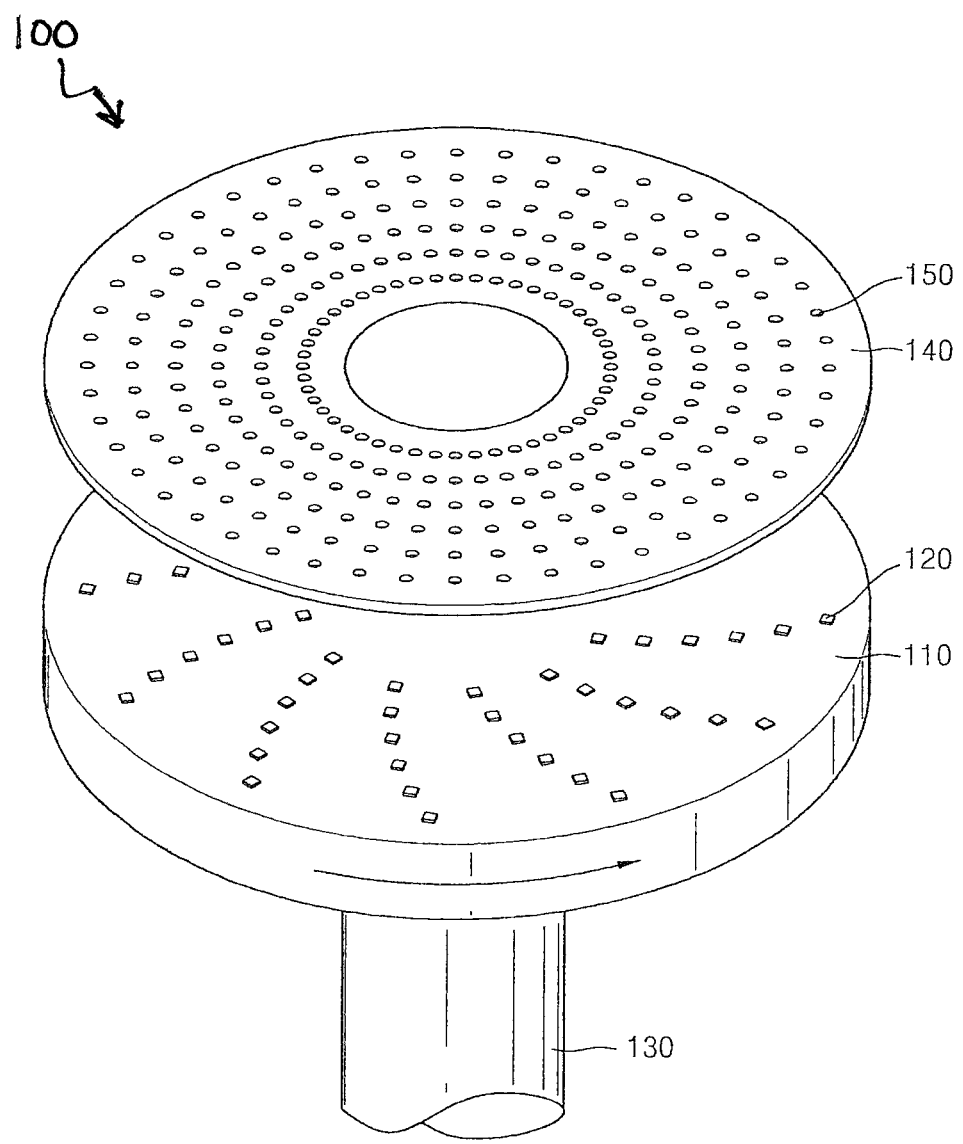
FIG. 1 is a schematic perspective view of a sequencing apparatus according to some example embodiments of the inventive concept.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Referring to FIG. 1, a sequencing apparatus 100 includes a stage 110 on which a plurality of optical heads 120 are arranged and a bio-disk 140 arranged on the stage 110.

A plurality of reaction regions 150 in which polymerization occurs between nucleic acid, such as DNA, and nucleotides are arranged on the bio-disk 140. Polymerase may be attached to the reaction regions 150. Polymerase may be used to form a double helix from a template strand by base-pairing interactions. Here, various types of nucleotides (e.g., 4 types of nucleotides) may be injected to the reaction regions 150. The nucleotides may include adenine A, guanine G, thymine T, and cytosine C.

The respective types of nucleotides may be marked with different fluorescent materials to be distinguished from each other. For example, adenine A may be marked with a first fluorescent material emitting light having a first wavelength, and guanine G may be marked with a second fluorescent material emitting light having a second wavelength. Furthermore, thymine T and cytosine C may be marked with a third fluorescent material and a fourth fluorescent material emitting light having a third wavelength and a fourth wavelength, respectively. Polymerase may attach nucleotides to a template strand and separate the fluorescent materials. Therefore, the base sequence of a template strand may be determined by detecting wavelengths of light emitted by the reaction regions 150 and arranging the detected wavelengths chronologically.

Polymerization of nucleic acid using polymerase may occur at a speed of about 1,000 times per second, for example. Therefore, to determine the base sequence of nucleic acid, it is necessary to perform detection 1000 or more times per second. However, in the method using an image capturing apparatus, it is impossible to capture images 1000 or more times per second, and thus an error ratio for determining the base sequence of nucleic acid is high.

According to some example embodiments of the inventive concept, a shaft 130 is connected to the center of the stage 110, and the shaft 130 may be rotated by a rotating device, e.g., a motor. The plurality of optical heads 120 may be arranged on the top surface of the stage 110. The optical heads 120 may be arranged in the circumferential direction around a center axis of the stage 110. In other words, the optical heads 120 may include first optical heads that are arranged to be a first distance apart from the center axis of the stage 110, second optical heads that are arranged to be a second distance apart from the center axis of the stage 110, third optical heads that are arranged to be a third distance apart from the center axis of the stage 110, and so on. Optical heads arranged to be a same distance apart from the center axis of the stage 110 may detect light emitted by a plurality of reaction regions corresponding to the optical heads.

The plurality of optical heads 120 may be arranged to be a same distance apart from the center axis, and the stage 110 revolves at a high speed. Therefore, one of the reaction regions 150 may be scanned by the optical heads 120 1,000 times or more per second. For example, the stage 110 may revolve 5,400 times, 7,200 times, or 15,000 times per minute. For example, in a hard disk drive (HDD), a disk may rotate at a rate of 5,400 rpm, 7,200 rpm, or 15,000 rpm. In other words, the stage 110 may revolve 90 times, 120 times, or 250 times per second. If it is assumed that a number of the plurality of optical heads 120 arranged to be a same distance apart from the center axis is 12, each of the reaction regions 150 may be scanned by the optical heads 120 1,080 times, 1,440 times, or 3,000 times. However, although it is assumed that the number of the plurality of optical heads 120 arranged to be a same distance apart from the center axis is 12, the number of the plurality of optical heads 120 arranged to be a same distance apart from the center axis may be less than 12 or greater than 12. For example, if the optical heads 120 are arranged to be 10 degrees apart from each other in a circumferential direction, a total of 36 optical heads 120 may be arranged to be a same distance apart from the center axis. In this case, each of the reaction regions 150 may be scanned from about 3,000 times to about 9,000 times per second. Therefore, the reaction regions 150 may be scanned faster than a reaction speed of polymerization of nucleic acid, and an error ratio for determining the base sequence of nucleic acid may be significantly reduced.

As shown in FIG. 1, the plurality of reaction regions 150 may be arranged on the bio-disk 140 to be at the same distances apart from the center axis of the bio-disk 140, respectively. Distances between the reaction regions 150 and the center axis of the bio-disk 140 may correspond to distances between the optical heads 120 and the center axis of the stage 110, respectively. Since nucleic acids are arranged in the reaction regions 150 of the bio-disk 140, it is necessary to maintain stability of the bio-disk 140. Therefore, the bio-disk 140 may not revolve and may be separated from the stage 110 and fixed.

Figure 2:
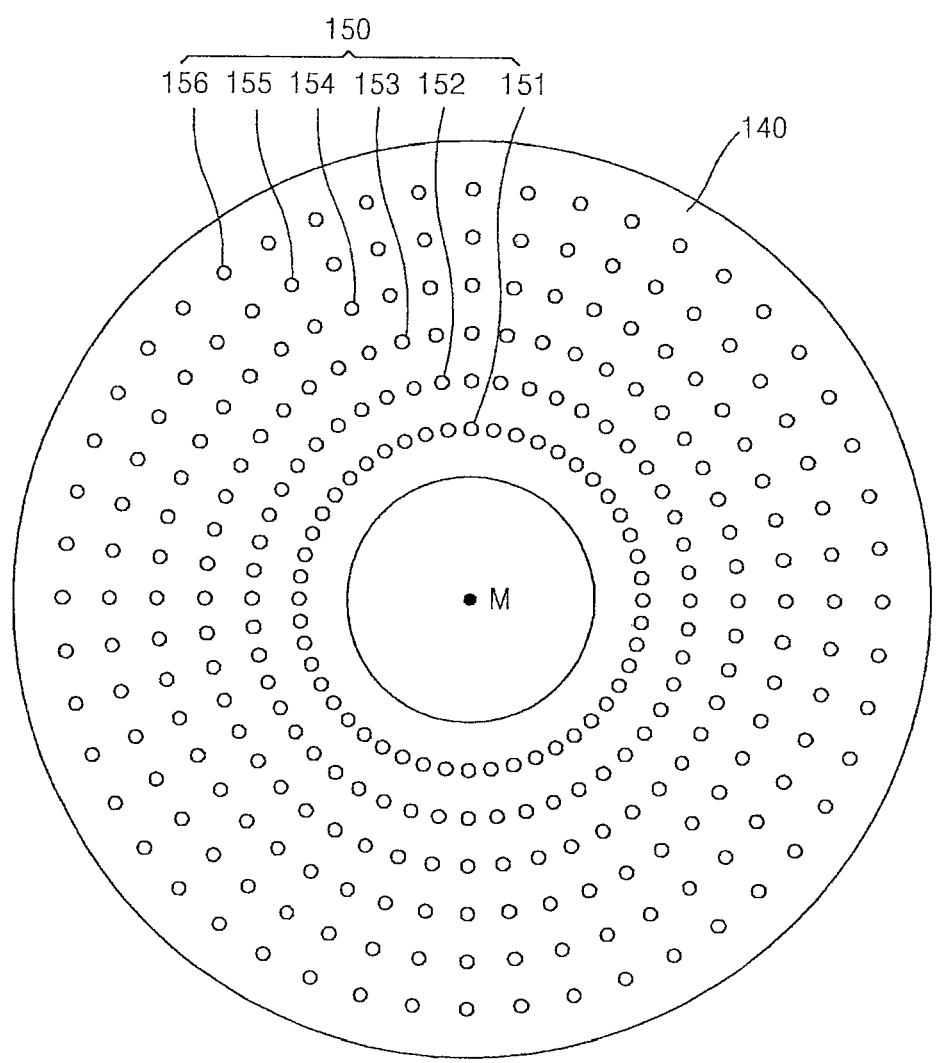
FIG. 2 is a plan view of a bio-disk shown in FIG. 1, in which an example arrangement of reaction regions on the bio-disk is shown.

FIG. 2 is a plan view of the bio-disk 140 shown in FIG. 1, in which an example arrangement of the reaction regions 150 on the bio-disk 140 is shown.

Referring to FIG. 2, the plurality of reaction regions 150 are arranged on the bio-disk 140. The reaction regions 150 may include first through sixth reaction regions 151 through 156. The first reaction regions 151 are arranged to be a first distance apart from the center M of the bio-disk 140 and are an equal distance apart from each other in the circumferential direction. According to some example embodiments of the inventive concept, the first reaction regions 151 are arranged to be about 7.5 degrees apart from each other around the center M in the circumferential direction. However, this is merely an example, and a greater or smaller number of the first reaction regions 151 may be arranged to be a first distance apart from the center M. A region in which the first reaction regions 151 are arranged may be referred to as a first track.

The second reaction regions 152 are arranged to be a second distance apart from the center M of the bio-disk 140 and are an equal distance apart from each other in the circumferential direction. As shown in FIG. 2, the second reaction regions 152 may also be arranged to be about 7.5 degrees apart from each other around the center M in the circumferential direction. A region in which the second reaction regions 152 are arranged may be referred to as a second track. In this regard, the third through sixth reaction regions 153, 154, 155, and 156 are respectively arranged to be third through sixth distances from the center M and may be equal distances apart from each other in the circumferential direction. Furthermore, regions in which the third through sixth reaction regions 153, 154, 155, and 156 are arranged may be referred to as third through sixth tracks, respectively.

FIG. 2 shows that each of the reaction regions 151 through 156 are arranged to be about 7.5 degrees apart from each other around the center M in the circumferential direction. However, to arrange a same number of the reaction regions 150 per unit area, the reaction regions 150 may be arranged to be smaller angles apart from each other as distances from the center M increase. For example, around the center M, the second reaction regions 152 may be about 6.5 degrees apart from each other in the circumferential direction, the third reaction regions 153 may be about 5.5 degrees apart from each other in the circumferential direction, the fourth reaction regions 154 may be about 4.5 degrees apart from each other in the circumferential direction, the fifth reaction regions 155 may be about 3.5 degrees apart from each other in the circumferential direction, and the sixth reaction regions 156 may be about 6.5 degrees apart from each other in the circumferential direction. Furthermore, tracks including reaction regions that are a same angle apart from each other may form a zone. For example, the first through third reaction regions 151 through 153 may be about 7.5 degrees apart from each other around the center M in the circumferential direction and form a first zone, whereas the fourth through sixth reaction regions 154 through 156 may be about 6 degrees apart from each other around the center M in the circumferential direction and form a second zone.

Although FIG. 2 shows that the first through sixth tracks are arranged, it is merely an example, and a greater or smaller number of tracks may be arranged on the bio-disk 140. Furthermore, although each of the first through sixth reaction regions 151 through 156 are arranged to be a same angle apart from each other, it is not necessary to arrange the first through sixth reaction regions 151 through 156 to be a same angle apart from each other.

Although FIG. 2 shows that the tracks are a same distance apart from each other in a radial direction, it is not necessary to arrange the tracks to be a same distance apart from each other in radial directions.

Figure 3:
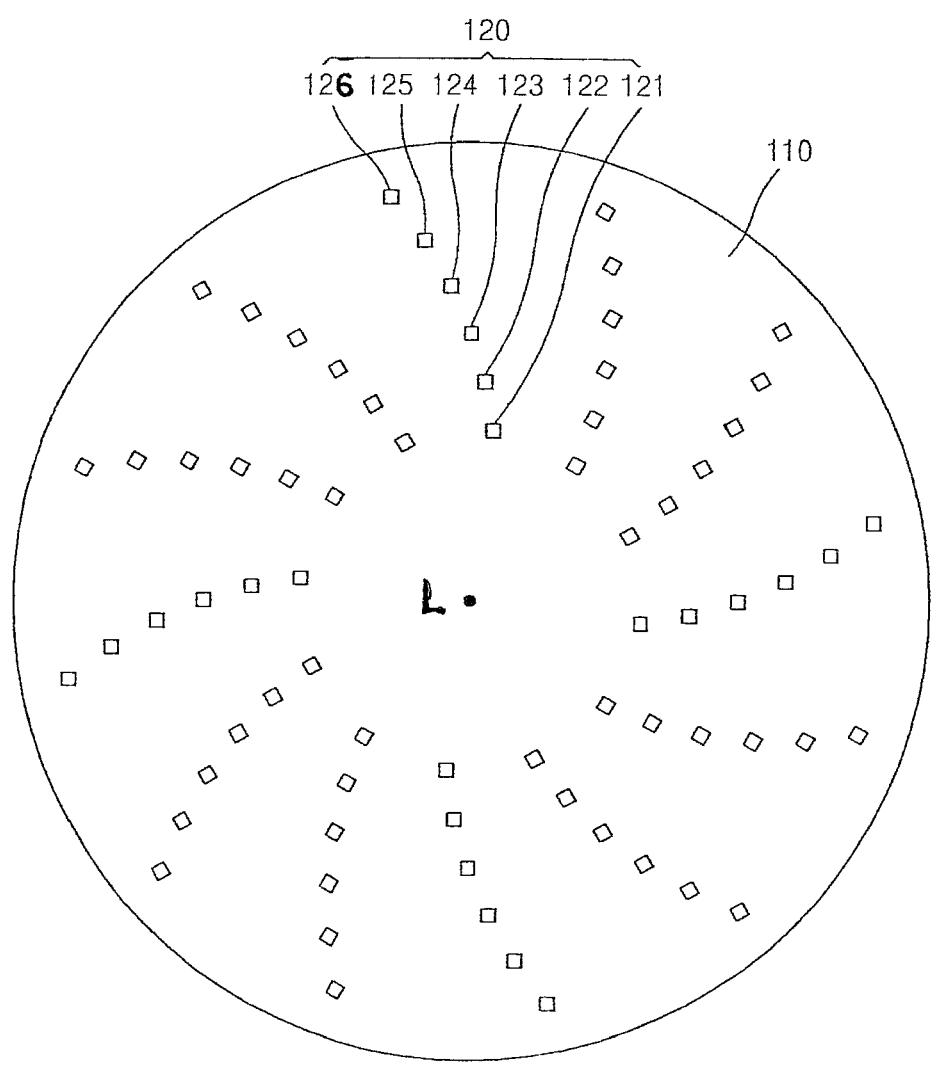
FIG. 3 is a plan view of a stage shown in FIG. 1, showing some example arrangements of optical heads on the stage.

FIG. 3 is a plan view of the stage 110 shown in FIG. 1, showing an example arrangement of the optical heads 120 on the stage 110.

Referring to FIG. 3, the optical heads 120 may include first through sixth optical heads 121 through 126, like the reaction regions 150. The first optical heads 121 are arranged to be the first distance apart from the center L of the stage 110 and may be an equal distance apart from each other in the circumferential direction. In this regard, the second through sixth optical heads 122 through 126 are arranged to be the second through sixth distances apart from the center L of the stage 110 and may be equal distances apart from each other in the circumferential direction, respectively.

Compared to the reaction regions 150, the optical heads 120 may be greater angles apart from each other around the center L in the circumferential direction. A number of the optical heads 120 may be smaller than a number of the reaction regions 150. If a number of the optical heads 120 is equal to or greater than a number of the reaction regions 150, the optical heads 120 may monitor the reaction regions 150 on a one-on-one basis. If the stage 110 revolves, a number of the optical heads 120 is smaller than a number of the reaction regions 150. However, if the stage 110 does not revolve, the optical heads 120 and the reaction regions 150 may match each other on an one-on-one basis.

The optical heads 120 may not be arranged in a radial direction and may be arranged to be slightly out of the radial direction for efficient utilization of spaces for forming and arranging the optical heads 120. However, the optical heads 120 may also be arranged in a radial direction according to some example embodiments of the inventive concept.

The plurality of first optical heads 121 may scan the plurality of first reaction regions 151 as the stage 110 revolves around the center L. Furthermore, the plurality of second optical heads 122 may scan the plurality of second reaction regions 152 as the stage 110 revolves around the center L. In this regard, the pluralities of third through sixth optical heads 123 through 126 may scan the pluralities of third through sixth reaction regions 153 through 156, respectively. Accordingly, all of the reaction regions 150 may be monitored by a smaller number of the optical heads 120.

Numbers, distances, and angles regarding the reaction regions 150 and the optical heads 120 shown in FIGS. 2 and 3 are merely examples, and example embodiments of the inventive concept are not limited thereto.

Figure 4:
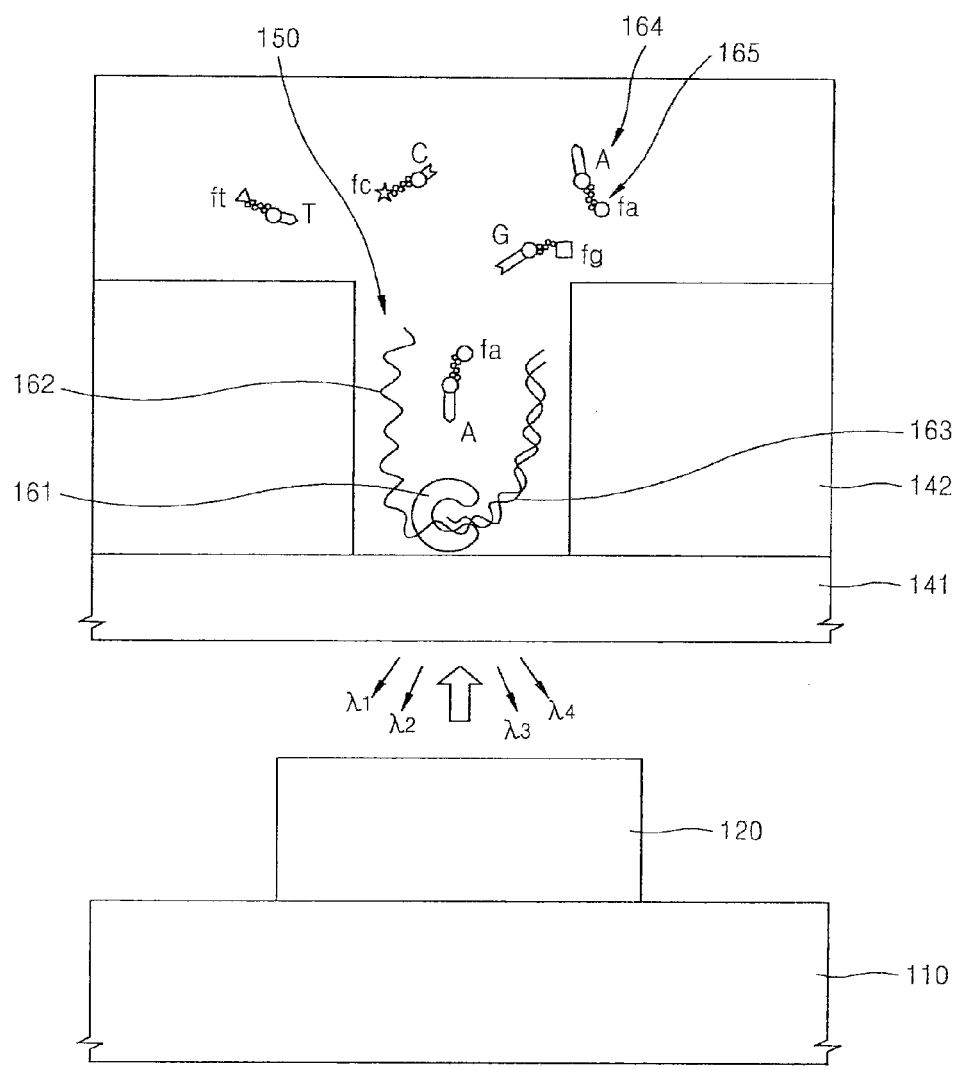
FIG. 4 is a magnified view showing a case in which an optical head that is moved by revolution of the stage is located below a reaction region, according to some example embodiments of the inventive concept.

FIG. 4 is a magnified view showing a case in which an optical head 120 that is moved by revolution of the stage 110 is located below a reaction region 150, according to some example embodiments of the inventive concept.

The optical head 120 is arranged on the stage 110. Since the stage 110 is revolved by the shaft 130, the optical head 120 moves in a direction parallel to a surface of the bio-disk 140. Since the optical head 120 and the reaction region 150 are respectively arranged in correspondence to each other, the optical head 120 is located below the reaction region 150.

The optical head 120 may emit light toward the reaction region 150. A fluorescent material 165 in the reaction regions 150 may receive light emitted by the optical heads 120 (no antecedent for singular optical head) and emit light having a different wavelength. The fluorescent material 165 in the reaction regions 150 may shift the wavelength of the light received from the optical heads 120 and emit light having a different wavelength. A degree of shifting a wavelength may vary according to type of the fluorescent material 165.

The bio-disk 140 may include a phototransmissive plate 141 and a non-phototransmissive plate 142 in which an opening is formed, where the opening may define the reaction region 150. The phototransmissive plate 141 may be formed of a phototransmissive material. For example, the phototransmissive plate 141 may be formed of glass or transparent plastic. The non-phototransmissive plate 142 may be formed of a material blocking transmittance of light. Although not shown in FIG. 4, an anti-reflection film may be formed on the bottom surface of a portion of the phototransmissive plate 141 overlapping the non-phototransmissive plate 142 to prevent light emitted by the optical head 120 from being reflected or a light absorbing film may be formed on the bottom surface of the portion of the phototransmissive plate 141 overlapping the non-phototransmissive plate 142 to absorb the light emitted by the optical head 120.

The cross-section of the reaction region 150 defined by the opening in the non-phototransmissive plate 142 may have a polygonal shape, such as a triangle, a rectangle, a pentagon, and so on, a circular shape, or an elliptical shape. If the cross-section of the reaction region 150 has a circular shape, the diameter of the cross-section of the reaction region 150 may be from dozens of nm to hundreds of nm.

Polymerase 161 may be attached to the top surface of the phototransmissive plate 141 exposed by the opening. A hydrophilic surface process may be performed on the top surface of the phototransmissive plate 141, such that the polymerase 161 is attached thereto.

The polymerase 161 generates a transfer strand 163 by attaching nucleotides 164 to a template strand 162 using base-pairing interactions. The transfer strand 163 is combined with the template strand 162 and forms a double helix. To provide the nucleotides 164 marked by the fluorescent material 165 to the reaction region 150, four types of the nucleotides 164 may be sufficiently arranged on top of the non-phototransmissive plate 142. The polymerase 161 may separate the fluorescent material 165 from the nucleotides 164 during polymerization.

For example, the nucleotides 164 may include adenine A, guanine G, thymine T, and cytosine C, where adenine A may be marked with a first fluorescent material fa, guanine G may be marked with a second fluorescent material fg, thymine T may be marked with a third fluorescent material ft, and cytosine C may be marked with a fourth fluorescent material fc. The first through fourth fluorescent materials fa, fg, ft, and fc may be referred to as the fluorescent materials 165 together. In the case of analyzing the base sequence of RNA, the nucleotides 164 may include uracil U instead of thymine T.

The first fluorescent material fa may shift the wavelength of a light emitted by the optical head 120 and may emit a light having a first wavelength $\lambda 1$. The second fluorescent material fg may shift the wavelength of a light emitted by the optical head 120 and may emit a light having a second wavelength $\lambda 2$. The third fluorescent material ft may shift the wavelength of a light emitted by the optical head 120 and may emit a light having a third wavelength $\lambda 3$. The fourth fluorescent material fc may shift the wavelength of a light emitted by the optical head 120 and may emit a light having a fourth wavelength $\lambda 4$.

Light emitted by the fluorescent materials 165 may be received by the optical heads 120. The optical heads 120 may determine types of nucleotides polymerized by the polymerase 161.

For example, for convenience of explanation, if it is assumed that one of the reaction regions 150 is monitored by one of the optical heads 120 and wavelengths of light received by the optical heads 120 are "$\lambda 1, \lambda 4, \lambda 2, \lambda 3, \lambda 3, \lambda 4, \lambda 1, \lambda 1, \lambda 2,$ and $\lambda 3$" in the order received, it may be determined that types of the nucleotides 164 combined with the template strand 162 are in the order of "A, C, G, T, T, C, A, A, G, and T." In this case, purine bases are combined with purine bases, whereas pyrimidine bases are combined with pyrimidine bases. In other words, adenine A is combined with guanine G, whereas thymine T is combined with cytosine C. Therefore, the template strand 162 is arranged in the order of "G, T, A, C, C, T, G, G, A, and C." Accordingly, the base sequence of the template strand 162 may be analyzed.

Figure 5:
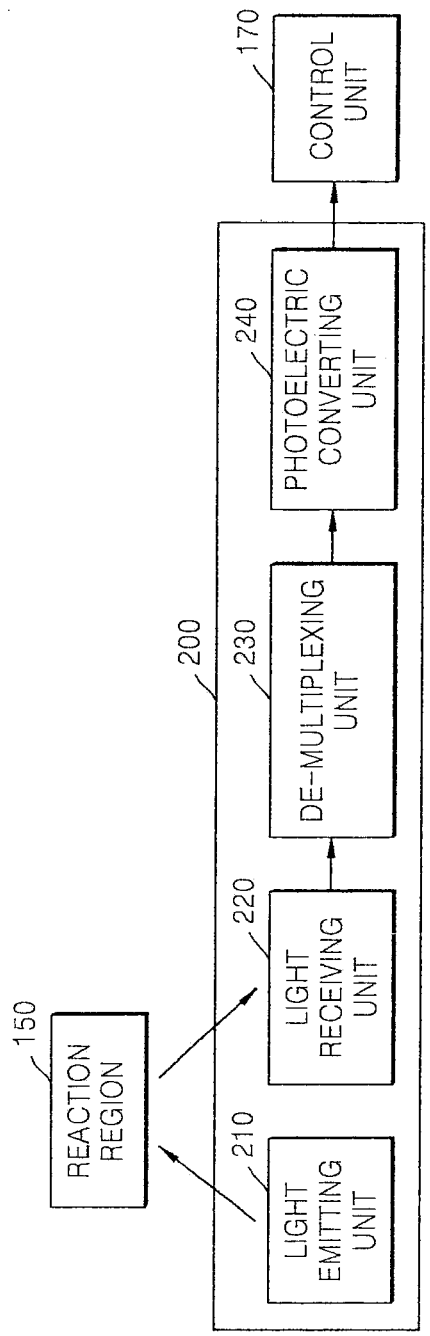
FIG. 5 is a block diagram of an optical head according to some example embodiments of the inventive concept.

FIG. 5 is a block diagram of an optical head 200 according to some example embodiments of the inventive concept.

Referring to FIG. 5, the optical head 200 includes a light emitting unit 210, a light receiving unit 220, a de-multiplexing unit 230, and a photoelectric converting unit 240. As shown in FIG. 4, the reaction region 150 may be arranged on the light emitting unit 210 and the light receiving unit 220.

Figure 7:
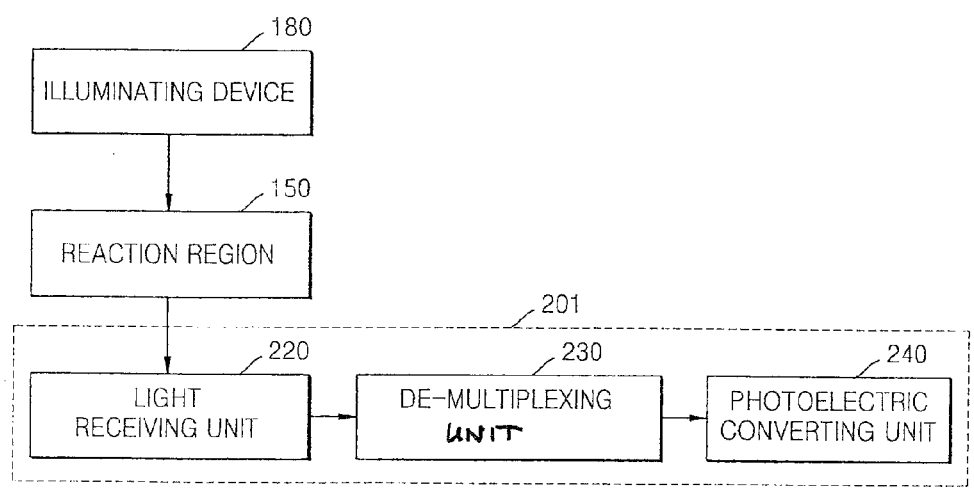
FIG. 7 block diagram of an optical head according to some example embodiments of the inventive concept.
Figure 8:
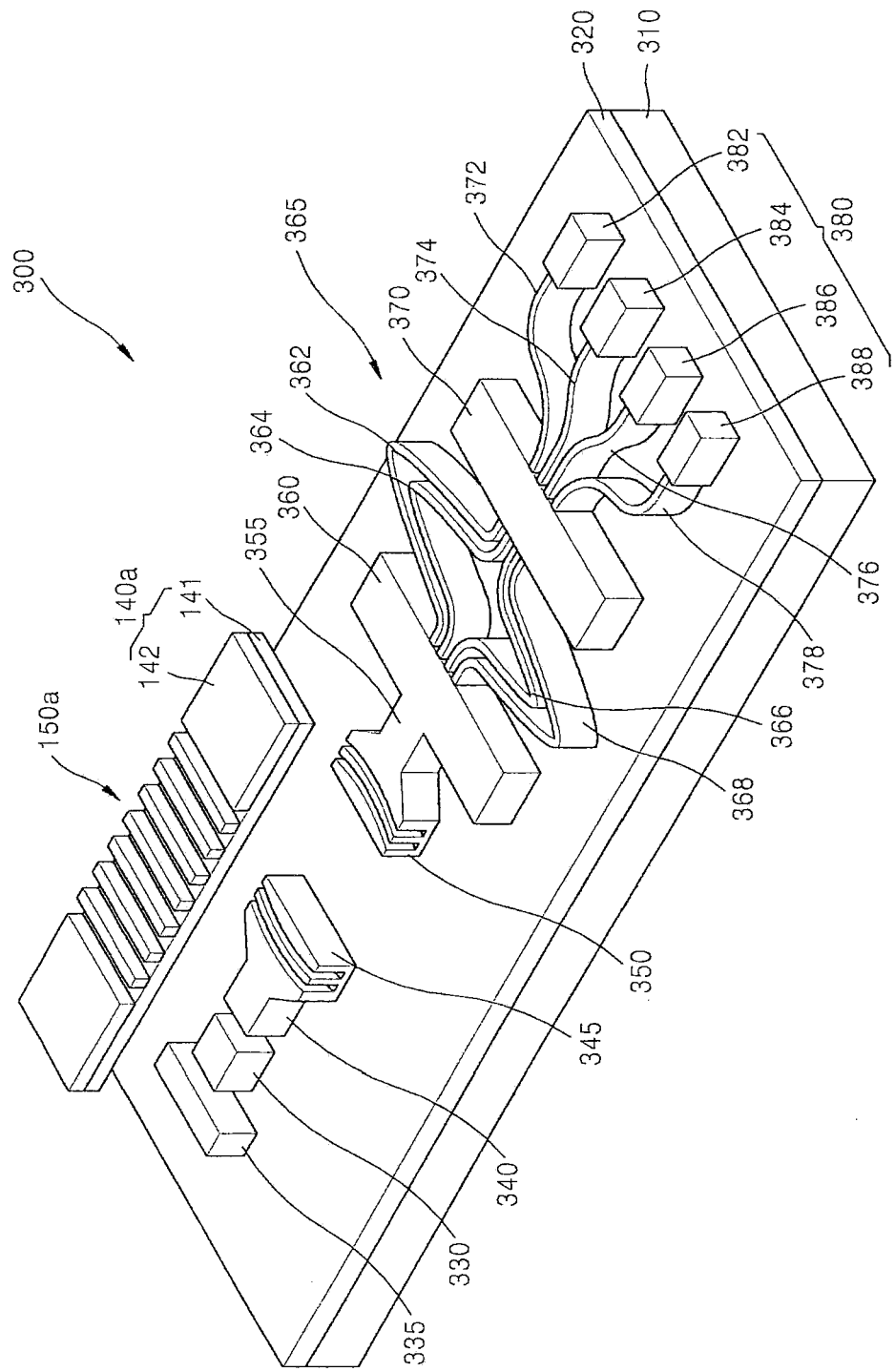
FIG. 8 is a schematic perspective view of an optical head according to some example embodiments of the inventive concept.

The light emitting unit 210 may emit light to illuminate a fluorescent material in the reaction region 150. The light emitting unit 210 may include a light emitting diode (LED). Although not shown, the light emitting unit 210 may include an LED and an orientating unit for orientating light emitted by the LED toward the reaction region 150. The orientating unit may be a mirror or may be a grating coupler as shown in FIGS. 7 and 8.

Furthermore, although not shown in FIG. 5, the optical head 200 may include a monitoring unit for monitoring whether the light emitting unit 210 emits light normally.

The light receiving unit 220 may receive light emitted by the fluorescent material in the reaction region 150. As described above, the light emitted by the reaction region 150 has one from among the first wavelength $\lambda 1$, the second wavelength $\lambda 2$, the third wavelength $\lambda 3$, and the fourth wavelength $\lambda 4$.

The de-multiplexing unit 230 may de-multiplex the light received by the light receiving unit 220 according to wavelengths. If the wavelength of the received light is the first wavelength $\lambda 1$, the de-multiplexing unit 230 may transmit the light to a first waveguide. If the wavelength of the received light is the second wavelength $\lambda 2$, the de-multiplexing unit 230 may transmit the light to a second waveguide. If the wavelength of the received light is the third wavelength $\lambda 3$, the de-multiplexing unit 230 may transmit the light to a third waveguide. If the wavelength of the received light is the fourth wavelength $\lambda 4$, the de-multiplexing unit 230 may transmit the light to a fourth waveguide. The de-multiplexing unit 230 may include a first light filter (not shown) which transmits light having the first wavelength $\lambda 1$ only, a second light filter (not shown) which transmits light having the second wavelength $\lambda 2$ only, a third light filter (not shown) which transmits light having the third wavelength $\lambda 3$ only, and a fourth light filter (not shown) which transmits light having the fourth wavelength $\lambda 4$ only. The first through fourth light filters may be band pass filters and may be formed of various types of light filters.

The photoelectric converting unit 240 may convert the light de-multiplexed by the de-multiplexing unit 230 to electrical signals. The photoelectric converting unit 240 may include four photo diodes in correspondence to the first through fourth waveguides that are split by the de-multiplexing unit 230. In other words, the photoelectric converting unit 240 may include a first photo diode connected to the first waveguide, a second photo diode connected to the second waveguide, a third photo diode connected to the third waveguide, and a fourth photo diode connected to the fourth waveguide.

In this case, if a light received by the light receiving unit 220 has the first wavelength $\lambda 1$, the second through fourth photo diodes do not react and only the first photo diode reacts, and thus only the first photo diode may generate electrical signals. In this regard, if a light received by the light receiving unit 220 has the second wavelength $\lambda 2$, only the second photo diode may generate electrical signals. If a light received by the light receiving unit 220 has the third wavelength $\lambda 3$, only the third photo diode may generate electrical signals. If a light received by the light receiving unit 220 has the fourth wavelength $\lambda 4$, only the fourth photo diode may generate electrical signals.

Electrical signals generated by the photoelectric converting unit 240 are transmitted to a control unit 170, and the control unit 170 may determine the base sequence of nucleic acids that are being polymerized in the reaction regions 150 by analyzing the electrical signals.

The optical head 200 shown in FIG. 5 may be used as the optical head 120 shown in FIG. 1.

The control unit 170 may be arranged in the stage 110 of FIG. 1. According to some example embodiments of the inventive concept, a first portion of the control unit 170 may be arranged in the stage 110, whereas a second portion of the control unit 170 may be arranged in an external control device. In this case, the first portion and the second portion of the control unit 170 may exchange data via data communication. For example, the first portion and the second portion of the control unit 170 may exchange data via wireless communication.

Furthermore, power for operating the control unit 170 and the optical heads 120 may be provided from outside via a cable or wireless power communication. Furthermore, a separate power supply unit for supplying the power may be arranged in the stage 110. The separate power supply unit may be a battery. Furthermore, the separate power supply unit for supplying the power may be a power generating device capable of converting a rotational force to electrical energy.

For example, by forming a magnetic field around the stage 110 and forming a closed circuit in the stage 110, the magnetic field transmitted through the closed circuit may change as the stage 110 revolves, and electrical energy may be generated by using an induced electromotive force according to the change in magnetic field.

Figure 6:
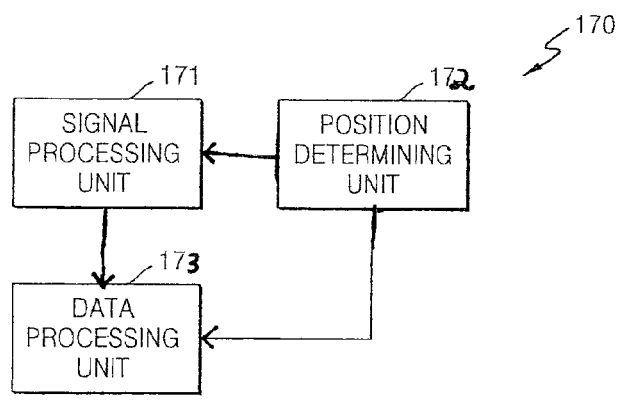
FIG. 6 is a block diagram for describing a control unit according to some example embodiments of the inventive concept.

FIG. 6 is a block diagram for describing the control unit 170 according to some example embodiments of the inventive concept.

Referring to FIG. 6, the control unit 170 may include a signal processing unit 171, a position determining unit 172, and a data processing unit 173.

The signal processing unit 171 may sample electrical signals generated by the photoelectric converting unit 240, convert the electrical signals to data, and transmit the data to the data processing unit 173. The signal processing unit 171 may individually sample electrical signals provided by the plurality of optical heads 200.

The position determining unit 172 may determine which one of the reaction regions 150 is being scanned by each of the optical heads 120. Since the arrangement of the reaction regions 150 in the bio-disk 140 is fixed and only the stage 110 revolves, position information may be generated by detecting a revolving state of the stage 110 by using a sensor attached to the shaft 130 or the stage 110. The position information may be transmitted to the data processing unit 173.

Furthermore, the position determining unit 172 may provide a sampling signal for determining a time point for sampling to the signal processing unit 171. The position determining unit 172 may detect a revolving speed of the stage 110, and a sampling interval between time points for sampling may be determined based on the revolving speed and an interval between the reaction regions 150 of the bio-disk 140 in the circumferential direction. Furthermore, as described above, the position determining unit 172 may calculate an accurate time point at which the optical head 200 is located below the reaction region 150 by using the position information. The position determining unit 172 may generate a sampling signal corresponding to a time point at which the optical head 200 is located below the reaction region 150 and provide the sampling signal to the signal processing unit 171. By using the sampling signal, false electrical signals due to noise and light-based electrical signals provided by the reaction regions 150 may be distinguished.

Furthermore, the position determining unit 172 may control the revolving speed of the stage 110. The revolving speed may be determined based on a period of time for a fluorescent material to emit light and a time interval between light emissions in one reaction region. For example, a revolving speed may be determined, such that a time interval between time points at which optical heads 120 that are adjacent to each other in the circumferential direction pass a particular point due to revolution is shorter than the shortest period of time for a fluorescent material to emit light The data processing unit 173 may analyze the base sequence of nucleic acids in each of the reaction regions 150 based on data provided by the signal processing unit 171 and position information provided by the position determining unit 172.

For example, it is assumed that the 8 reaction regions 150 are arranged in the first track and are scanned by using the two optical heads 200. It is assumed that the data as shown below is transmitted by the signal processing unit 171.

It is assumed that a portion of data D1 generated based on electrical signals generated by the first optical head and a portion of data D2 generated based on electrical signals generated by the second optical head are as shown below.

D1=1432 2313 4223 1124 3221 1234 1212 3424 1334 1144 1421 3212 1334 4421 4322 4124

D2=4323 3112 1414 1123 3341 2142 3212 2313 1242 1232 1142 4324 4324 3223 2412 4232

Here, values at the same positions are scanned at the same points of time, respectively. Furthermore, a value "1" of data means that light having the first wavelength λ1 is emitted by the reaction region 150, a value "2" of data means that light having the second wavelength λ2 is emitted by the reaction region 150, a value "3" of data means that light having the third wavelength λ3 is emitted by the reaction region 150, and a value "4" of data means that light having the fourth wavelength λ4 is emitted by the reaction region 150.

Furthermore, according to position information provided by the position determining unit 172, the data processing unit 173 may determine that the first value of the data D1 is the value of data obtained as the first optical heads scan the first reaction regions. Since the second optical heads are arranged at an opposite side of the first optical heads around the center of the stage 110, it may be determined that the first value of the data D2 is the value of data obtained as the second optical heads scan the fifth reaction regions.

In this case, the data processing unit 173 may determine the base sequence of nucleic acids in each of the reaction regions 150 based on the data D1 and D2.

The data D1 is data acquired by the first optical heads via repeated scanning of the first through eight reaction regions. Furthermore, the data D2 is data acquired by the second optical heads via repeated scanning of the fifth through eight reaction regions and then the first through fourth reaction regions. Furthermore, the first reaction region is alternately scanned by the first optical heads and the second optical heads. Therefore, data corresponding to light emitted by the first reaction region includes the first value of the data D1, the fifth value of the data D2, the ninth value of the data D1, the thirteenth value of the data D2, the seventeenth value of the data D1, and so on. In other words, the data corresponding to the light emitted by the first reaction region is "1," "3," "4," "1," "3," "2," "1," "2," "1," "1," "1," "4," "1," "3," "4," and "4." Therefore, types of nucleotides polymerized to form nucleic acids in the first reaction region are "A," "T," "C," "A," "T," "G," "A," "G," "A," "A," "A," "C," "A," "T," "C," and "C" in the order stated. Furthermore, the data processing unit 173 may determine that the base sequence of nucleic acids in the first reaction region is "G," "C," "T," "G," "C," "A," "G," "A," "G," "G," "G," "T," "G," "C," "T," and "T," using base-pairing interactions.

Similarly, the base sequences of nucleic acids in the second through eighth reaction regions may be analyzed; however, detailed descriptions thereof will be omitted here.

In some example embodiments of the inventive concept, it is assumed that new nucleotides are combined with a template strand every time an optical head passes through a reaction region, for convenience of explanation. In reality, when an optical head passes through a reaction region, no nucleotide may be combined with a template strand, no light may be emitted, and no electrical signal may be generated. Alternatively, light emitted by a fluorescent material as one nucleotide is combined with a template strand may be detected by a plurality of optical heads. In this case, a speed of scanning reaction regions may be very high due to a high revolving speed of a stage.

However, in a case where a scanning speed is very high as stated above, after previous nucleotides are combined with a template strand, at least one optical head may pass through a reaction region before new nucleotides are combined with the template strand, and thus the base sequence may be analyzed without any error by analyzing the base sequence based on data not used to generate any electrical signal.

For example, in a case where a scanning speed is very high as stated above, a result of analyzing the base sequence may be "G," "N," "C," "N," "N," "T," "T," "N," "N," "N," "G," "N," "N," "C," "N," "A," "N," "N," "N," "G," "N," "A," "N," "N," "N," "G," "G," "N," "G," "N," "N," "G," "N," "N," "N," "T," "N," "G," "N," "N," "C," "C," "N," "N," "T," "N," "N," "N," and "T," for example. Here, the value "N" indicates that no electrical signal is generated.

In this case, repeated bases between "N" and "N" are results of repeatedly scanning light emitted when one nucleotide is combined with a template strand, it may be determined that not the same nucleotides, but one nucleotide, is combined with the template strand. In other words, data including values "N," "T," "T," and "N" indicates that one "T" is combined with a template strand, whereas data including values "N," "T," "N," "T," and "N" indicates that two "T"s are combined with the template strand.

When the above data is processed in the same regard, the data processing unit 173 may determine that the data indicates the base sequence of "G," "C," "T," "G," "C," "A," "G," "A," "G," "G," "G," "T," "G," "C," "T," and "T," as in the above example embodiments.

The base sequence of nucleic acids analyzed by the data processing unit 173 may be provided to outside via wireless communication or may be stored in a separate storage medium, such as a flash memory, and read out from the storage device by an external computing device.

FIG. 7 block diagram of an optical head 201 according to some example embodiments of the inventive concept.

The optical head 201 of FIG. 7 is substantially identical to the optical head 200 of FIG. 5, except that the light emitting unit 210 is omitted in the optical head 201 of FIG. 7. The functions of the light emitting unit 210 in the example embodiment shown in FIG. 5 may be performed by a separate illuminating device 180. The illuminating device 180 may be arranged at an opposite side of the optical head 201 around the reaction region 150. In other words, in the example embodiment shown in FIG. 4, the illuminating device 180 may be arranged above the bio-disk 140 and may emit light downward from above the reaction region 150. Alternatively, the one illuminating device 180 may illuminate the plurality of reaction regions 150.

FIG. 8 is a schematic perspective view of an optical head 300 according to some example embodiments of the inventive concept.

Referring to FIG. 8, the optical head 300 may include a substrate 310. The substrate 310 may be a glass substrate, a plastic substrate, or a silicon substrate. The substrate 310 may be a part of the stage 110 of FIG. 1 or may be attached to the stage 110.

A cladding material layer 320 may be arranged on the substrate 310. The cladding material layer 320 prevents light signals from being leaked to outside via total reflection from optical devices, such as waveguides formed on the cladding material layer 320. Here, the optical devices may be formed of a core material, and a refractive index of the core material may be greater than that of the cladding material layer 320. If the substrate 310 is formed of silicon, the cladding material layer 320 may be a silicon oxide layer. If the cladding material layer 320 is a silicon oxide layer, the silicon oxide layer may be formed via chemical vapor deposition (CVD) or thermal oxidation. Furthermore, if the cladding material layer 320 is a silicon oxide layer, the core material may be silicon. For example, the core material may be amorphous silicon, poly silicon, or monocrystalline silicon.

At least one of an LED 330, a monitoring photo diode 335, a first waveguide 340, a first grating coupler 345, a second grating coupler 350, a second waveguide 355, an arrayed waveguide grating 365, and a photoelectric converting unit 380 may be arranged on the cladding material layer 320.

The LED 330 may emit light according to electrical signals. The LED 330 may be a laser diode. The monitoring photo diode 335 is used to monitor whether light is emitted by the LED 330. If the LED 330 emits light, the monitoring photo diode 335 may generate an electrical signal.

The first waveguide 340 may transmit light emitted by the LED 330 to the first grating coupler 345. The first grating coupler 345 may orientate the light received from the first waveguide 340 toward a reaction region 150a. The first grating coupler 345 may be a focusing grating coupler.

As shown in FIG. 8, the reaction region 150a is defined by an opening in a bio-disk 140a and is substantially the same as the reaction region 150 described above with reference to FIG. 4. The bio-disk 140a shown in FIG. 8 corresponds to a portion of the bio-disk 140 of FIG. 1 and FIG. 8 shows that the section of the reaction region 150a has a rectangular shape. However, example embodiments of the inventive concept are not limited thereto.

The second grating coupler 350 receives light emitted due to polymerization in the reaction region 150a and transmits the light to the second waveguide 355. The second waveguide 355 is connected to the arrayed waveguide grating 365, and the light transmitted to the second waveguide 355 is separated according to wavelengths as the light passes through the arrayed waveguide grating 365.

The arrayed waveguide grating 365 may include a first slab waveguide 360 connected to the second waveguide 355, first through fourth waveguide gratings 362, 364, 366, and 368 which are connected to the first slab waveguide 360 and have different lengths, a second slab waveguide 370 to which the first through fourth waveguide gratings 362, 364, 366, and 368 are connected, and first through fourth output waveguides 372, 374, 376, and 378 which are connected to the second slab waveguide 370 from different locations. Light having the first wavelength λ1 may be transmitted only to the first output waveguide 372, light having the second wavelength λ2 may be transmitted only to the second output waveguide 374, light having the third wavelength λ3 may be transmitted only to the third output waveguide 376, and light having the fourth wavelength λ4 may be transmitted only to the fourth output waveguide 378. Therefore, the arrayed waveguide grating 365 may function as a band pass filter with respect to the first through fourth wavelengths λ1, λ2, λ3, and λ4.

The first output waveguide 372 may be connected to a first photo diode 382, the second output waveguide 374 may be connected to a second photo diode 384, the third output waveguide 376 may be connected to a third photo diode 386, and the fourth output waveguide 378 may be connected to a fourth photo diode 388. As a result, if light emitted by the reaction region 150a has the first wavelength λ1, the first photo diode 382 will generate an electrical signal. Furthermore, the second photo diode 384 will operate if the light has the second wavelength λ2, the third photo diode 386 will operate if the light has the third wavelength λ3, and the fourth photo diode 388 will operate if the light has the fourth wavelength λ4. The first through fourth photo diodes 382, 384, 386, and 388 may be included in the photoelectric converting unit 380.

The first waveguide 340, the first grating coupler 345, the second grating coupler 350, the second waveguide 355, and the arrayed waveguide grating 365 may be formed of silicon, e.g., amorphous silicon, crystalline silicon, or monocrystalline silicon. To form the optical devices by using monocrystalline silicon, amorphous silicon or crystalline silicon may be deposited onto the cladding material layer 320 via a semiconductor process, such as CVD. Next, monocrystalline silicon may be formed by crystallizing the deposited amorphous silicon or crystalline silicon via solid phase epitaxial (SPE) growth or laser epitaxial growth (LEG). By patterning the monocrystalline silicon via a photolithographic process and an etching process, the first waveguide 340, the first grating coupler 345, the second grating coupler 350, the second waveguide 355, and the arrayed waveguide grating 365 may be formed.

Although not shown in FIG. 8, the LED 330, the monitoring photo diode 335, the first waveguide 340, the first grating coupler 345, the second grating coupler 350, the second waveguide 355, the arrayed waveguide grating 365, and the photoelectric converting unit 380 may be covered with a cladding material that is the same as that of the cladding material layer 320.

As described above, the optical head 300 shown in FIG. 8 may include silicon photonic devices. Therefore, mass productions of the optical head 300 may be available via a semiconductor fabricating process with high precision and reduced cost.

Figure 9:
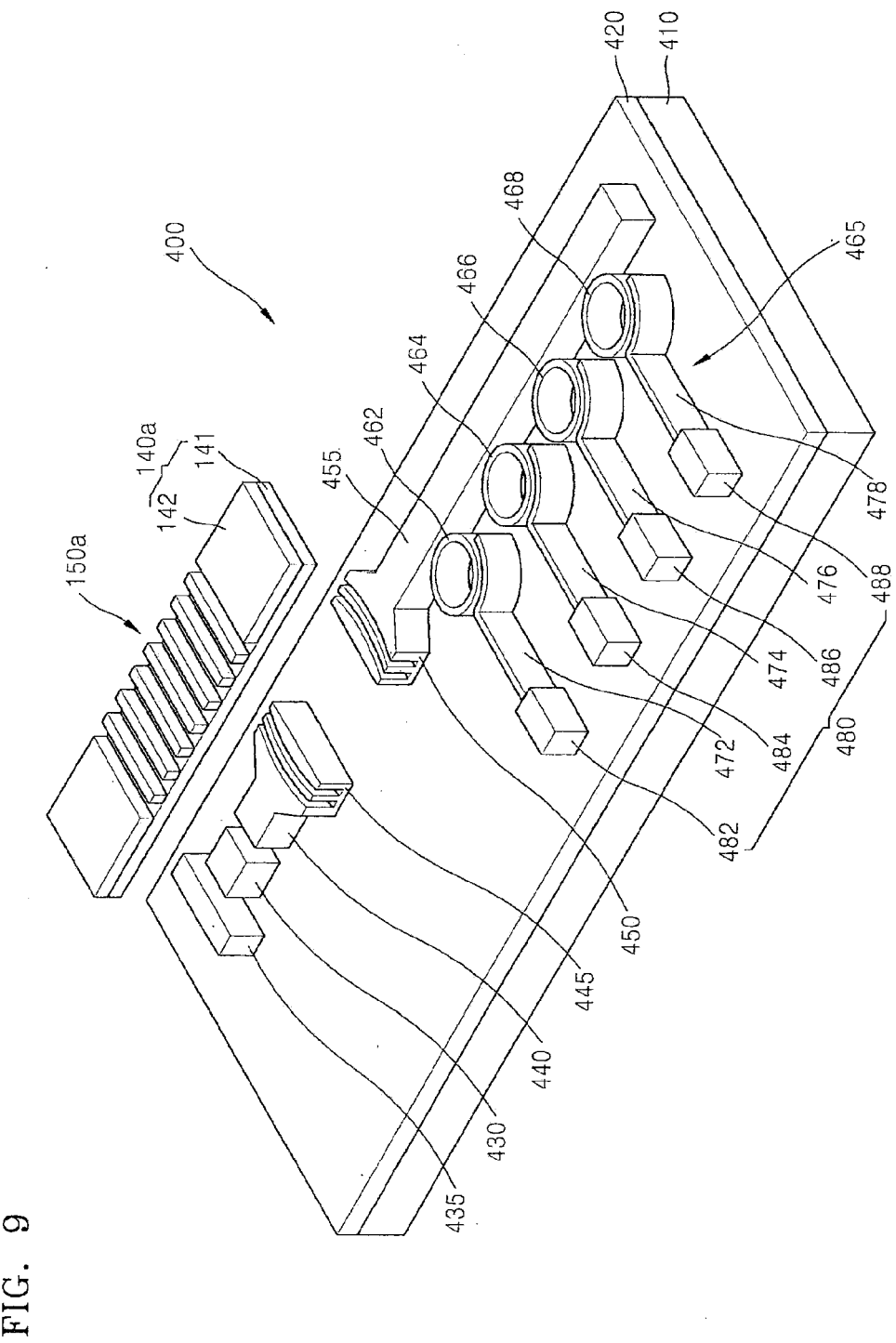
FIG. 9 is a schematic perspective view of an optical head according to some example embodiments of the inventive concept.

FIG. 9 is a schematic perspective view of an optical head 400 according to some example embodiments of the inventive concept.

Referring to FIG. 9, the optical head 400 may include a substrate 410, a cladding material layer 420, an LED 430, a monitoring photo diode 435, a first waveguide 440, a first grating coupler 445, a second grating coupler 450, a second waveguide 455, and a photoelectric converting unit 480. The substrate 410, the cladding material layer 420, the LED 430, the monitoring photo diode 435, the first waveguide 440, the first grating coupler 445, the second grating coupler 450, the second waveguide 455, and the photoelectric converting unit 480 are substantially identical to the substrate 310, the cladding material layer 320, the LED 330, the monitoring photo diode 335, the first waveguide 340, the first grating coupler 345, the second grating coupler 350, the second waveguide 355, and the photoelectric converting unit 380 described above with reference to FIG. 8, respectively. Therefore, detailed descriptions thereof will not be repeated here.

The optical head 400 may include a circular filter 465. The circular filter 465 may include first through fourth ring structures 462, 464, 466, and 468 and first through fourth output waveguides 472, 474, 476, and 478. The first ring structure 462 is arranged to be a distance corresponding to the first wavelength $\lambda 1$ apart from the second waveguide 455 and the first output waveguide 472. The second ring structures 464 is arranged to be a distance corresponding to the second wavelength $\lambda 2$ apart from the second waveguide 455 and the second output waveguide 474. The third ring structures 466 is arranged to be a distance corresponding to the third wavelength $\lambda 3$ apart from second waveguide 455 and the third output waveguide 476. The fourth ring structures 468 is arranged to be a distance corresponding to the fourth wavelength $\lambda 4$ apart from the second waveguide 455 and the fourth output waveguide 478.

Therefore, if light having the first wavelength $\lambda 1$ passes through the second waveguide 455, the light is transmitted only to the first ring structure 462 and the first output waveguide 472. If light having the second wavelength $\lambda 2$ passes through the second waveguide 455, the light is transmitted only to the second ring structure 464 and the second output waveguide 474. If light having the third wavelength $\lambda 3$ passes through the second waveguide 455, the light is transmitted only to the third ring structure 466 and the third output waveguide 476. If light having the fourth wavelength $\lambda 4$ passes through the second waveguide 455, the light is transmitted only to the fourth ring structure 468 and the fourth output waveguide 478.

Light transmitted to the first output waveguide 472 is converted to electrical signals by the first photo diode 482. Light transmitted to the second output waveguide 474 is converted to electrical signals by the second photo diode 484. Light transmitted to the third output waveguide 476 is converted to electrical signals by the third photo diode 486. Light transmitted to the fourth output waveguide 478 is converted to electrical signals by the fourth photo diode 488.

The converted electrical signals are transmitted to the control unit described above with reference to FIG. 6 and the data processing unit in the control unit analyzes the base sequence of nucleic acids.

While example embodiments have been particularly shown and described, it will be understood by those of ordinary skill in the art that various changes in form and details may be made therein without departing from the spirit and scope of the present invention as defined by the following claims.

What is claimed is:

1. An optical head, comprising:
    a light emitting unit configured to emit light toward a reaction region in which nucleic acids are polymerized;
    a light receiving unit configured to receive the light emitted by the light emitting unit and that has one from among first through fourth wavelengths;
    a de-multiplexing unit configured to de-multiplex the light received by the light receiving unit according to wavelengths thereof; and
    a plurality of photoelectric converting units configured to convert the de-multiplexed light to electrical signals;
    wherein the de-multiplexing unit comprises an arrayed waveguide grating configured to separate the light received by the light receiving unit according to the wavelengths thereof,
    wherein the arrayed waveguide grating comprises:
        a first slab waveguide connected to a second grating coupler via a first waveguide;
        first through fourth waveguide gratings that are connected to the first slab waveguide and have different lengths;
        a second slab waveguide to which the first through fourth waveguide gratings are connected; and
        first through fourth output waveguides that are connected to the second slab waveguide from different locations; and
    wherein the first through fourth output waveguides are respectively connected to the plurality of photoelectric converting units.

2. The optical head of claim 1, wherein the light emitting unit comprises:
    a light emitting diode (LED) configured to emit the light toward the reaction region;
    a first grating coupler configured to orient the light emitted by the LED toward the reaction region; and
    a second waveguide configured to transmit the light emitted by the LED to the first grating coupler.

3. The optical head of claim 2, wherein the light receiving unit comprises:
    a second grating coupler configured to receive light emitted by the reaction region; and the first waveguide configured to transmit the light received by the second grating coupler to the de-multiplexing unit.

4. The optical head of claim 1, wherein the de-multiplexing unit further comprises a circular filter configured to separate the light received by the light receiving unit according to the wavelengths thereof.

5. The optical head of claim 4, wherein the light receiving unit comprises the first grating coupler configured to receive light emitted by the reaction region, and wherein the circular filter comprises:
- the first waveguide connected to a second grating coupler;
- four ring structures that are respective distances, corresponding to the first through fourth wavelengths, apart from the first waveguide; and
- four second waveguides that are respective distances, corresponding to the first through fourth wavelengths, apart from the four ring structures and are connected to the plurality of photoelectric converting units.

* * * * *